United States Patent
Zheng et al.

(10) Patent No.: US 11,826,461 B2
(45) Date of Patent: Nov. 28, 2023

(54) ANTI-HAIR LOSS AND HAIR GROWTH INTEGRATED CORE-SHELL MICRONEEDLE PATCH

(71) Applicants: Tangyi Holdings (Shenzhen) Limited, Shenzhen (CN); Healthina Stem Cell Industry Platform (Tianjin) Limited, Tianjin (CN)

(72) Inventors: Bin Zheng, Shenzhen (CN); Yulin Cao, Shenzhen (CN); Bowen Li, Shenzhen (CN); Wei Sun, Shenzhen (CN); Shixiang Cheng, Shenzhen (CN)

(73) Assignees: TANGYI HOLDINGS (SHENZHEN) LIMITED, Shenzhen (CN); HEALTHINA STEM CELL INDUSTRY PLATFORM (TIANJIN) LIMITED, Tianjin (CN)

( * ) Notice: Subject to any disclaimer, the term of this patent is extended or adjusted under 35 U.S.C. 154(b) by 112 days.

(21) Appl. No.: 17/503,768

(22) Filed: Oct. 18, 2021

(65) Prior Publication Data
US 2023/0071574 A1  Mar. 9, 2023

(30) Foreign Application Priority Data
Sep. 6, 2021 (CN) .......................... 202111039620.2

(51) Int. Cl.
| | | |
|---|---|---|
| *A61M 3/00* | (2006.01) | |
| *A61K 9/00* | (2006.01) | |
| *A61K 35/28* | (2015.01) | |
| *C12N 5/00* | (2006.01) | |
| *A61M 37/00* | (2006.01) | |
| *B29C 41/04* | (2006.01) | |
| *B29C 41/38* | (2006.01) | |
| *C12N 5/0775* | (2010.01) | |
| *B29L 31/00* | (2006.01) | |

(52) U.S. Cl.
CPC ............ *A61K 9/0021* (2013.01); *A61K 35/28* (2013.01); *A61M 37/0015* (2013.01); *B29C 41/04* (2013.01); *B29C 41/38* (2013.01); *C12N 5/0663* (2013.01); *A61M 2037/0023* (2013.01); *A61M 2037/0053* (2013.01); *B29K 2883/00* (2013.01); *B29L 2031/7544* (2013.01)

(58) Field of Classification Search
CPC ...... A61K 9/0021; A61K 35/28; A61K 38/43; A61K 9/7023; A61K 47/32; A61M 37/0015; A61M 2037/0023; A61M 2037/0053; A61M 2037/0046; B29C 41/04; B29C 41/38; C12N 5/0663; B29K 2883/00; B29L 2031/7544; A61P 17/14
See application file for complete search history.

(56) References Cited

U.S. PATENT DOCUMENTS

2023/0015942 A1* 1/2023 Lee .................... A61L 27/34

* cited by examiner

*Primary Examiner* — Amber R Stiles
(74) *Attorney, Agent, or Firm* — PORUS IP LLC

(57) ABSTRACT

The present invention discloses a nano-armored single cell product, comprising a liposome and probiotics encapsulated by the liposome, wherein the probiotics are fermented to produce gamma-aminobutyric acid (GABA) that alleviates the activation of an inflammatory response in substantia nigra inducedin a MPTP induced PD model, thus mitigating an inflammatory injury to dopaminergic neurons in substantia nigra and having a neuroprotective effect; encapsulation of the probiotics by the liposome can protect the probiotics from strong acids and digestive enzymes in gastric acid.

5 Claims, 1 Drawing Sheet

ANTI-HAIR LOSS AND HAIR GROWTH INTEGRATED CORE-SHELL MICRONEEDLE PATCH

FIELD OF THE INVENTION

The present invention relates to the technical field of microneedle patch, in particular to an anti-hair loss and hair growth integrated core-shell microneedle patch.

BACKGROUND OF THE INVENTION

Hair loss is a common human disease for various reasons, such as aging, diseases and drugs. According to the estimation, more than 50% of general population suffer from the hair loss disease, the current clinical treatment of hair loss mainly depends on hair follicle transplantation, but it is limited by high surgery cost, high invasiveness and donor shortage. In contrast, non-invasive induction of inherent hair follicle regeneration is one of the effective methods for solving hair loss.

Generally, human hair follicles will undergo a cyclic process of quiescence, regeneration and degradation, this period is regulated by hair follicle stem cells which can be activated by signals mainly from their niches and enter from other resting stages into a transitional stage of resting stage-growing stage. The exosome is an extracellular vesicle secreted by various cell types and loaded with various substances such as proteins, lipids and nucleic acids, and the exosome participates in mediating cellular reactions and biological processes, such as tissue repair and regeneration.

The imbalance of hair follicle niches is the main cause that affects hair loss, which is usually caused by insufficient blood vessels or oxidative stress in the microenvironment around hair follicles. Insufficient angiogenesis in the bald area of a patient with hair loss will lead to insufficient transportation of nutrient substances and affect the transformation of cytokines and other bioactive molecules into hair follicles, thus limiting the transformation of hair follicles from a terminal stage to a growth stage; in addition to insufficient angiogenesis, oxidative stress can also destroy the innate antioxidation defense mechanism, thus inducing apoptosis in hair follicles; in addition, excessive active oxygen can trigger premature aging of dermal papilla cells, and then inhibit the transformation from the resting stage to the growth stage of hair follicles mediated by an androgen signal and an activation signal. Oxidative stress is correlated with angiogenesis defects, and the accumulation of active oxygen has been proved to block angiogenic reaction and increase dysfunction of blood vessel. Therefore, the dual regulation of oxidative stress and vascularization around hair follicles provides a potential treatment method for promoting hair regeneration.

SUMMARY OF THE INVENTION

The present invention aims to provide an anti-hair loss and hair growth integrated core-shell microneedle patch to solve the above problems of serious hair loss and difficult hair growth for human beings.

In order to achieve the above purpose, the present invention provides an anti-hair loss and hair growth integrated core-shell microneedle patch, comprising a backing and a core-shell microneedle array attached to one side of the backing, the core-shell microneedle array comprises a plurality of microneedles arranged on the backing to form an array, each microneedle comprises a shell substrate material and an internal core, and the shell substrate material is loaded with nano-enzyme for removing excessive active oxygen;

A preparation method of anti-hair loss and hair growth integrated core-shell microneedle patch, comprising the following steps, (1) Preparation of a microneedle shell structure: dissolving nano-enzyme in an aqueous solution of the shell substrate material to form a mixture, centrifuging the mixture to remove air and depositing the mixture on a female microneedle mold, then centrifuging the female microneedle mold so that the mixture flows into forming holes of the female microneedle mold, using and pressing a male microneedle mold matched with the female microneedle mold into the female microneedle mold, putting it into a drier for drying at room temperature, and then unloading the male microneedle mold, so that the microneedle shell structure is prepared; the female microneedle mold is a polydimethylsiloxane (PDMS) micromold, the spacing between tips and the tip height of the male microneedle mold are the same as those of the female microneedle mold, and the base area of the female microneedle mold is twice as much as that of the male microneedle mold;

(2) Preparation of a microneedle core structure: culturing human bone marrow mesenchymal stem cells, isolating the mesenchymal stem cell-derived exosomes from a cell culture medium with an exosome isolation reagent, adding a keratin solution containing cysteine and exosomes into a groove of the microneedle shell structure, removing excessive keratin solution through a plastic scraper, and putting the keratin solution in a drier for drying at room temperature;

(3) Preparation of the backing: applying a solution containing a backing material to the surface of the bottom end of the microneedle and the upper surface of the female microneedle mold not covered by the microneedle to form backing solution layers, the backing material is crosslinked to form a continuous backing, and finally the microneedle is attached to the backing;

Preparation of the anti-hair loss and hair growth integrated core-shell microneedle patch: drying and curing the core-shell microneedle array on the backing, and unloading the female microneedle mold to form the anti-hair loss and hair growth integrated core-shell microneedle patch;

The anti-hair loss and hair growth integrated core-shell microneedle patch is used to alleviate and treat androgenic hair loss with hair follicle niche imbalance caused by excessive active oxygen and insufficient vascularization of the microenvironment around hair follicles, and used to promote head hair follicle regeneration.

Preferably, the anti-hair loss and hair growth integrated core-shell microneedle patch is used to promote head hair follicle regeneration.

Preferably, the shell substrate material is a soluble polymer and comprises one or more of polyvinyl alcohol, trehalose, hyaluronic acid, polylactic acid, galactose, polyvinylpyrrolidone, polyethylene glycol diacrylate, silk fibroin, methacrylate gelatin and carboxy methyl cellulose. The shell substrate material in the present invention is a substrate material commonly used for preparing microneedle patches in the art, but polyvinyl alcohol is preferred in order to ensure that the microneedle prepared by the method of the present invention has a certain mechanical strength, polyvinyl alcohol has the function of skin protection, can be applied to acceleration of wound healing, has good solubility, biocompatibility and mechanical strength, and is selected as a substrate component of the microneedle patch. In addition, polyvinyl alcohol can be degraded by active oxygen to consume free radicals, thus mitigating oxidative stress in the microenvironment around follicles to protect cells from death.

Preferably, the backing comprises one or more of polyethylene glycol diacrylate, silk fibroin, methacrylate gelatin, carboxy methyl cellulose, trehalose, hyaluronic acid, polylactic acid-glycolic acid copolymer, polylactic acid, galactose, polyvinylpyrrolidone and polyvinyl alcohol. The backing in the present invention can only be the backing commonly used in the preparation of microneedles in the art, but polyvinylpyrrolidone is preferred considering the mechanical strength and flexibility of the formed backing.

Preferably, the internal core comprises mesenchymal stem cell-derived exosomes.

Preferably, the nano-enzyme comprises one or more of monoatomic nano-enzyme, complex nano-enzyme, catalase-like enzyme and peroxidase-like enzyme. The nano-enzyme may be the traditional nano-enzyme, for example, $Fe_3O_4$, $CeO_2$ and the like, but it is not limited to the traditional nano-enzyme, it may be monatomic nano-enzyme, complex nano-enzyme and the like, and the nano-enzyme has the simulated activity of catalase (CAT) and superoxide dismutase (SOD).

Preferably, each microneedle has a tip end and a bottom end, the tip end is far away from the backing, and the microneedle is attached to the backing via the bottom end.

The sizes and shapes of the backing and the microneedle in the present invention are not specifically limited and can be selected in a wide range according to the used part of the anti-hair loss and hair growth integrated microneedle patch and the diseases to be treated.

Therefore, the anti-hair loss and hair growth integrated core-shell microneedle patch of the present invention using the above-mentioned structure has the following beneficial effects that:

(1) The core-shell microneedle patch can effectively get nano-enzyme into the skin, thus removing excessive active oxygen, stimulating the remodeling of capillaries in the bald area and accelerating hair regeneration.
(2) After the shell substrate material is degraded, the core-shell microneedle patch can release the exosomes contained in the internal core to promote the growth of hair follicles.
(3) The core-shell microneedle patch can exhibit accelerated hair regeneration in mouse models with androgenic hair loss at a low dosing frequency without causing significant skin damage.
(4) According to the present invention, the microneedles are prepared by molding a microneedle template, which has the advantages of simple method, convenient operation, low price, reusability, no high technical requirements, easy control of the basic appearance of the microneedle array, high safety and suitability for popularization.

The technical solution of the present invention will be described in further detail below through the drawings and embodiment.

In the figures: 100. core-shell microneedle patch; 110. microneedle; 120. backing; 200. female microneedle mold; 201. forming hole; 202. upper surface.

DESCRIPTION OF THE INVENTION

The technical solution of the present invention will be further described below through the drawings and embodiment.

The present invention provides an anti-hair loss and hair growth integrated core-shell microneedle patch, comprising a backing 120 and a core-shell microneedle array attached to one side of the backing 120, wherein the core-shell microneedle array comprises a plurality of microneedles 110 arranged on the backing 120 to form an array, each microneedle 110 comprises a shell substrate material and an internal core, and the shell substrate material is loaded with nano-enzyme for removing excessive active oxygen. The internal core comprises mesenchymal stem cell-derived exosomes. The nano-enzyme comprises one or more of monoatomic nano-enzyme, complex nano-enzyme, catalase-like enzyme and peroxidase-like enzyme. The shell substrate material and the internal core form a core-shell structure, and when the core-shell microneedle patch 100 is used, the shell substrate material and the internal core act on the scalp successively to promote hair growth.

Figure 1:
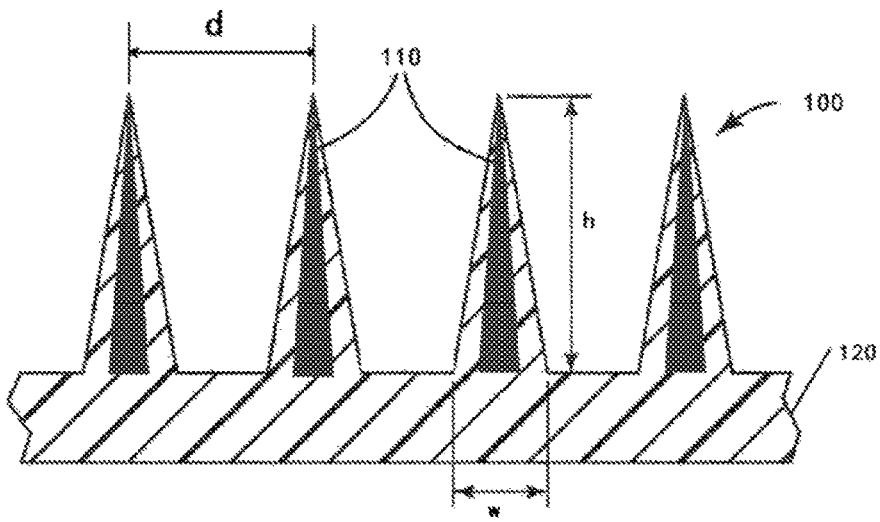
FIG. 1 is a side view of the core-shell microneedle patch of the embodiment of the present invention.
Figure 2:
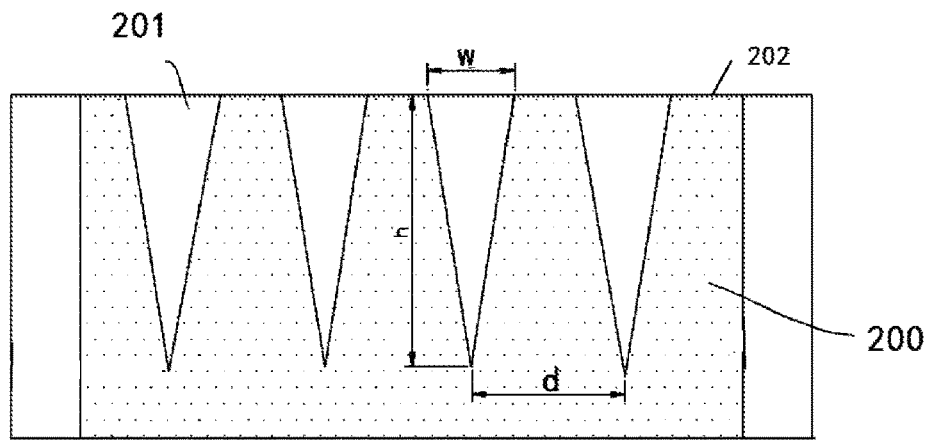
FIG. 2 is a side view of the female microneedle mold of the embodiment of the present invention.

Each microneedle 110 has a tip end and a bottom end, the tip end is far away from the backing, and the microneedle 110 is attached to the backing 120 via the bottom end. The three-dimensional shape of the microneedle 110 is not specifically limited, which is either cylindrical, conical, truncated cone shaped or a combination thereof, or in the shape of a regular or irregular cone, conoid, triangular pyramid, quadrangular pyramid or more advanced pyramid and other shapes, and the cone, conoid, triangular pyramid, quadrangular pyramid or more advanced pyramid may be a regular cone or oblique cone. As shown in FIG. 1, the diameter of the bottom end of the microneedle 110 is preferably not less than 100 μm, more preferably 100-500 μm; if the diameter is less than 100 μm, the mechanical strength of the microneedle is insufficient, the microneedle is easy to break; if the diameter is greater than 500 μm, the microneedles used in some parts on an animal body or human body will leave large holes on the skin and cause the problem of affecting the skin beauty and healing; the distance between the tip ends of adjacent microneedles is preferably 300-800 μm, and within this spacing, the core-shell microneedle patch 100 can achieve optimal effects in many aspects such as nano-enzyme and exosome release efficiency after penetrating to the depth of stratum corneum. During preparation of the microneedles, a template method is used, the female microneedle mold and the male microneedle mold are used, as shown in FIG. 2, the female microneedle mold 200 comprises an upper surface 202 and forming holes 201 extending downward on the upper surface 202, the forming holes 201 are matched with the shape of the microneedles 110, the forming holes 201 also have tip ends and bottom ends, the tip end of the female microneedle mold is far away from the upper surface, the bottom end of the female microneedle mold is flush with the upper surface, the height, bottom end width and tip end spacing of the forming holes are either the same as or greater than the height, bottom end width and tip end spacing of the microneedles, in the latter case, the forming holes 201 will not be filled up with the formed microneedles, and both the upper surface of the female microneedle mold and the inner surface of the forming holes can be coated with anti-adhesion layers to facilitate mold unloading.

Note that those skilled in the art have the ability to make appropriate choices on the shape, size and the like of the microneedles of the anti-hair loss and hair growth integrated core-shell microneedle patch 100 of the present invention according to the actual application.

The shell substrate material is a soluble polymer and comprises one or more of polyvinyl alcohol, trehalose, hyaluronic acid, polylactic acid, galactose, polyvinylpyrrolidone, polyethylene glycol diacrylate, silk fibroin, methacrylate gelatin and carboxy methyl cellulose. The shell substrate material in the present invention is a substrate material commonly used for preparing microneedle patches in the art, but polyvinyl alcohol is preferred in order to ensure that the microneedle prepared by the method of the present invention has a certain mechanical strength, polyvinyl alcohol has the function of skin protection, can be applied to acceleration of wound healing, has good solubility, biocompatibility and mechanical strength, and is selected as a substrate component of the microneedle patch. In addition, polyvinyl alcohol can be degraded by active oxygen to consume free radicals, thus mitigating oxidative stress in the microenvironment around follicles to protect cells from death.

The backing comprises one or more of polyethylene glycol diacrylate, silk fibroin, methacrylate gelatin, carboxy methyl cellulose, trehalose, hyaluronic acid, polylactic acid-glycolic acid copolymer, polylactic acid, galactose, polyvinylpyrrolidone and polyvinyl alcohol. The backing in the present invention can only be the backing commonly used in the preparation of microneedles in the art, but polyvinylpyrrolidone is preferred considering the mechanical strength and flexibility of the formed backing.

Embodiment 1

A preparation method of anti-hair loss and hair growth integrated core-shell microneedle patch, comprising the following steps,
(1) Preparation of a microneedle shell structure: dissolving nano-enzyme in an aqueous solution of the shell substrate material to form a mixture, centrifuging the mixture to remove air and depositing the mixture on a polydimethylsiloxane (PDMS) female microneedle mold, then centrifuging the PDMS female microneedle mold, so that the mixture flows into forming holes of the female microneedle mold, using and pressing a male microneedle mold matched with the PDMS female microneedle mold into the female microneedle mold, putting it into a drier and holding for 2 hours at room temperature, and using polyvinyl alcohol as the shell substrate material;
(2) Preparation of a microneedle core structure: culturing human bone marrow mesenchymal stem cells, isolating the mesenchymal stem cell-derived exosomes from a cell culture medium with an exosome isolation reagent, adding a keratin solution containing cysteine and exosomes into a groove of the microneedle shell structure, removing excessive keratin solution through a plastic scraper, and putting the keratin solution in a drier for drying at room temperature until the keratin solution is completely dry;
(3) Preparation of the backing: applying a solution containing a backing material to the surface of the bottom end of the microneedle and the upper surface of the female microneedle mold not covered by the microneedle to form backing solution layers, the backing material is crosslinked to form a continuous backing, finally the microneedle is attached to the backing, and using polyvinylpyrrolidone for the backing;
(4) Preparation of the anti-hair loss and hair growth integrated core-shell microneedle patch: drying and curing the core-shell microneedle array on the backing, and unloading the female microneedle mold to form the anti-hair loss and hair growth integrated core-shell microneedle patch.

Figure 3:
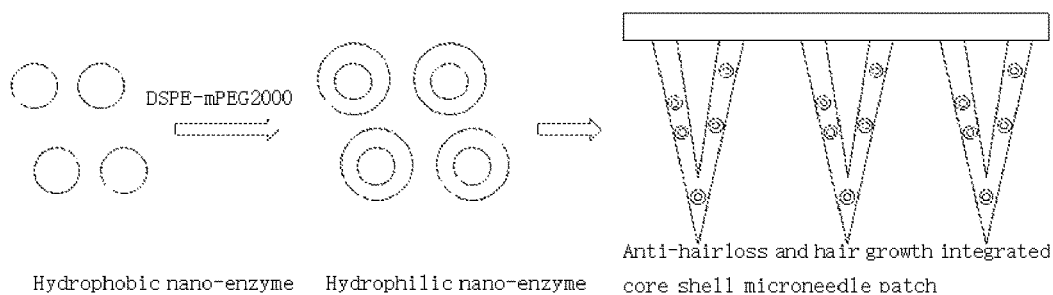
FIG. 3 is a schematic diagram of the preparation process of the core-shell microneedle patch of the embodiment of the present invention.

As can be seen from FIG. 3, hydrophobic nano-enzyme treated by DSMP-mPEG2000 is transformed into hydrophilic nano-enzyme, and evenly dispersed in the microneedle shell structure formed by the shell substrate material.

Comparative Example 1

The difference from the above preparation process of Embodiment 1 is that the internal core in Comparative Example 1 does not contain exosomes.

The therapeutic effect of the anti-hair loss and hair growth integrated core-shell microneedle patch is tested, the mouse models with androgenic hair loss are built by topical administration of testosterone solution every day for 28 days, five groups of mouse models with androgenic hair loss are used to test the effect of the microneedle patch, one of the groups is a model group to which only testosterone solution is applied, the blank microneedle patch, the nano-enzyme microneedle patch (prepared in Comparative Example 1) and the core-shell microneedle patch (prepared in Embodiment 1) are used on the other three groups of mouse models with androgenic hair loss respectively, the patches are used for 15 days and replaced every three days, a Minoxidil solution is used for the last group and applied every day for 13 consecutive days. The measurement results are shown in Table 1, and the therapeutic effect of the anti-hair loss and hair growth integrated core-shell microneedle patch is judged by scoring the hair diameter, percentage of Ki67 positive cells and hair cycle.

TABLE 1

Therapeutic effect of anti-hair loss and hair growth integrated core-shell microneedle patch

| | Model Group | Blank Microneedle Patch group | Minoxidil Group | Nano-enzyme Microneedle Patch | Core-shell Microneedle Patch |
|---|---|---|---|---|---|
| Hair diameter (μm) | 6 | 6 | 11 | 11 | 11 |
| Ki67 positive cells (%) | 18 | 20 | 20 | 60 | 68 |
| Hair cycle score | 5 | 16 | 22 | 45 | 50 |

As can be seen from the data in Table 1, the core-shell microneedle patch of Embodiment 1 prepared in the present invention can achieve a good therapeutic effect for treating hair loss, the Ki67 positive cells are significantly increased, cell proliferation is accelerated, which are good for hair growth; compared with Minoxidil, a drug used to treat hair loss, the microneedles exhibit the effect of accelerating hair regeneration in the mouse models with androgenic hair loss at a low usage frequency, and will not lead to significant skin damage. After the core-shell microneedle patch is applied to the mice with androgenic hair loss, the tip ends of the microneedles firstly stimulate the hair loss area mechanically to remodel capillaries in the hair loss area, then the shell substrate material is rapidly degraded, the nano-enzyme loaded by the shell substrate material is passively released to remove active oxygen and promote angiogenesis in the microenvironment around hair follicles, thus promoting hair regeneration; then the exosomes are also released and transported to the hair follicle niches to improve pigmentation and promote hair regeneration, and therefore, the microneedle patch in the present invention can gradually improve the hair follicle environment in the hair loss area step by step and promote hair growth through the core-shell structure of the microneedle patch.

Therefore, the present invention uses the anti-hair loss and hair growth integrated core-shell microneedle patch in the above-mentioned structure, wherein the shell substrate material is rapidly degraded after the microneedle patch is applied to human skin, the nano-enzyme loaded by the shell substrate material can be passively released to remove active oxygen and promote angiogenesis in the microenvironment around hair follicles, the internal core of the microneedle is loaded with mesenchymal stem cell-derived exosomes, and the internal exosomes are released and conveyed to hair follicle niches after the shell substrate material is degraded, so that improvement of pigmentation and promotion of hair regrowth are possible.

Finally, it should be specified that: the above embodiment is only used to illustrate rather than to limit the technical solution of the present invention, the present invention is described in detail with reference to a better embodiment, but those of ordinary skill in the art should understand that: they can still make modifications or equivalent replacements of the technical solution of the present invention, and these modifications or equivalent replacements cannot make the modified technical solution depart from the spirit and scope of the technical solution of the present invention either.

The invention claimed is:

1. An anti-hair loss and hair growth integrated core-shell microneedle patch, comprising a backing and a core-shell microneedle array attached to one side of the backing, wherein:
   the core-shell microneedle array comprises a plurality of microneedles arranged on the backing to form an array,
   each microneedle comprises a shell substrate material and an internal core,
   the shell substrate material is loaded with a nano-enzyme for removing excessive active oxygen, and the internal core comprises mesenchymal stem cell-derived exosomes;
   wherein the anti-hair loss and hair growth integrated core-shell microneedle patch is prepared by the following steps:
   preparing a microneedle shell structure, comprising steps of:
   dissolving the nano-enzyme in an aqueous solution of the shell substrate material to form a mixture, centrifuging the mixture to remove air and depositing the mixture on a female microneedle mold, then centrifuging the female microneedle mold so that the mixture flows into forming holes of the female microneedle mold, using and pressing a male microneedle mold matched with the female microneedle mold into the female microneedle mold to obtain a pressed female microneedle mold with the male microneedle mold, putting the pressed female microneedle mold with the male microneedle mold into a drier for drying at room temperature, and then unloading the male microneedle mold, so that the microneedle shell structure is prepared, wherein the female microneedle mold is a polydimethylsiloxane (PDMS) micromold, a spacing between tips and a tip height of the male microneedle mold are the same as those of the female microneedle mold, and a base area of the female microneedle mold is twice as much as that of the male microneedle mold;
   preparing a microneedle core structure, comprising steps of: culturing human bone marrow mesenchymal stem cells in a cell culture medium, isolating the mesenchymal stem cell-derived exosomes from the cell culture medium with an exosome isolation reagent, adding a keratin solution containing cysteine and exosomes into a groove of the microneedle shell structure, removing excessive keratin solution through a plastic scraper, and putting the keratin solution in a drier for drying at room temperature, so that the plurality of microneedles are obtained;
   preparing the backing, comprising steps of: applying a solution containing a backing material to a surface of a bottom end of each microneedle of the plurality of microneedles and an upper surface of the female microneedle mold not covered by each microneedle to form backing solution layers, the backing material being crosslinked to form a continuous backing, and attaching the plurality of microneedles to the backing, so that the core-shell microneedle array is obtained;
   preparing the anti-hair loss and hair growth integrated core-shell microneedle patch, comprising steps of: drying and curing the core-shell microneedle array on the backing, and unloading the female microneedle mold to form the anti-hair loss and hair growth integrated core-shell microneedle patch; wherein
   the anti-hair loss and hair growth integrated core-shell microneedle patch is used to alleviate and treat androgenic hair loss with hair follicle niche imbalance caused by excessive active oxygen and insufficient vascularization of the microenvironment around hair follicles, and used to promote head hair follicle regeneration.

2. The anti-hair loss and hair growth integrated core-shell microneedle patch according to claim 1, wherein the shell substrate material is a soluble polymer and comprises one or more of polyvinyl alcohol, trehalose, hyaluronic acid, polylactic acid, galactose, polyvinylpyrrolidone, polyethylene glycol diacrylate, silk fibroin, methacrylate gelatin and carboxy methyl cellulose.

3. The anti-hair loss and hair growth integrated core-shell microneedle patch according to claim 1, wherein the backing comprises one or more of polyethylene glycol diacrylate, silk fibroin, methacrylate gelatin, carboxy methyl cellulose, trehalose, hyaluronic acid, polylactic acid-glycolic acid copolymer, polylactic acid, galactose, polyvinylpyrrolidone and polyvinyl alcohol.

4. The anti-hair loss and hair growth integrated core-shell microneedle patch according to claim 1, wherein the nano-enzyme comprises one or more of a monoatomic nano-enzyme, a complex nano-enzyme, a catalase-like enzyme and a peroxidase-like enzyme.

5. The anti-hair loss and hair growth integrated core-shell microneedle patch according to claim 1, wherein each microneedle has a tip end and a bottom end, the tip end is oriented away from the backing, and the microneedle is attached to the backing via the bottom end.

* * * * *